(12) United States Patent
Staudner

(10) Patent No.: US 7,419,496 B2
(45) Date of Patent: Sep. 2, 2008

(54) TROCAR WITH RETRACTABLE CUTTING SURFACE

(76) Inventor: Rupert A. Staudner, 780 - 122nd St. Ocean, Marathon, FL (US) 33050

(*) Notice: Subject to any disclaimer, the term of this patent is extended or adjusted under 35 U.S.C. 154(b) by 119 days.

(21) Appl. No.: 10/910,054

(22) Filed: Aug. 3, 2004

(65) Prior Publication Data

US 2006/0030870 A1    Feb. 9, 2006

(51) Int. Cl.
    *A61B 17/34* (2006.01)
(52) U.S. Cl. ..................................... 606/185
(58) Field of Classification Search .............. 606/130, 606/167, 170–172, 182, 185, 168; 600/164.12; 604/164.12
    See application file for complete search history.

(56) References Cited

U.S. PATENT DOCUMENTS

| | | | |
|---|---|---|---|
| 4,535,773 A | 8/1985 | Yoon | |
| 4,556,059 A * | 12/1985 | Adamson, Jr. | 128/207.29 |
| 4,601,710 A | 7/1986 | Moll | |
| 4,654,030 A | 3/1987 | Moll et al. | |
| 4,906,595 A | 3/1990 | van der Plas et al. | |
| 4,931,042 A | 6/1990 | Holmes et al. | |
| 5,030,206 A | 7/1991 | Lander | |
| 5,104,382 A | 4/1992 | Brinkerhoff et al. | |
| 5,114,407 A | 5/1992 | Burbank | |
| 5,116,353 A | 5/1992 | Green | |
| 5,152,754 A | 10/1992 | Plyley et al. | |
| 5,158,552 A | 10/1992 | Borgia et al. | |
| 5,215,526 A | 6/1993 | Deniega et al. | |
| 5,224,952 A | 7/1993 | Deniega et al. | |
| 5,226,426 A | 7/1993 | Yoon | |
| 5,246,425 A | 9/1993 | Hunsberger et al. | |
| 5,261,891 A | 11/1993 | Brinkerhoff et al. | |
| 5,267,965 A | 12/1993 | Deniega | |
| 5,275,583 A | 1/1994 | Crainich | |
| 5,290,243 A | 3/1994 | Chodorow et al. | |
| 5,290,304 A | 3/1994 | Storace | |
| 5,290,310 A | 3/1994 | Yoon | |
| 5,295,993 A | 3/1994 | Green | |
| 5,312,354 A | 5/1994 | Allen et al. | |
| 5,314,417 A | 5/1994 | Stephens et al. | |
| 5,318,580 A | 6/1994 | Gresl, Jr. | |
| 5,318,585 A | 6/1994 | Guy et al. | |
| 5,324,268 A | 6/1994 | Yoon | |
| 5,330,432 A | 7/1994 | Yoon | |
| 5,336,176 A | 8/1994 | Yoon | |
| 5,338,305 A | 8/1994 | Plyley et al. | |
| 5,342,382 A | 8/1994 | Brinkerhoff et al. | |
| 5,346,459 A | 9/1994 | Allen | |

(Continued)

*Primary Examiner*—Todd E. Manahan
*Assistant Examiner*—Elizabeth Houston
(74) *Attorney, Agent, or Firm*—Bachman & LaPointe, P.C.

(57) ABSTRACT

A trocar having a cutting shaft with a cutting surface at a distal end. The cutting shaft moves longitudinally with respect to an obturator such that in one position the cutting surface is in an exposed position suitable for application of a piercing force. Upon interruption of the piercing force to the cutting surface, the cutting surface moves longitudinally with respect to the obturator such that the cutting surface is in a retracted position within the obturator. The trocar may include a first spring urging the cutting surface to an exposed position and a second spring urging the cutting surface to a retracted position. The second spring has a slightly stronger biasing force than the first spring to bias the cutting surface to the retracted position.

9 Claims, 7 Drawing Sheets

U.S. PATENT DOCUMENTS

| | | |
|---|---|---|
| 5,356,421 A | 10/1994 | Castro |
| 5,360,405 A | 11/1994 | Yoon |
| 5,364,365 A | 11/1994 | Wortrich |
| 5,364,372 A | 11/1994 | Danks et al. |
| 5,366,445 A | 11/1994 | Haber et al. |
| 5,387,197 A | 2/1995 | Smith et al. |
| 5,399,167 A | 3/1995 | Deniega |
| 5,401,247 A | 3/1995 | Yoon |
| 5,423,760 A | 6/1995 | Yoon |
| 5,423,770 A | 6/1995 | Yoon |
| 5,431,635 A | 7/1995 | Yoon |
| 5,441,513 A | 8/1995 | Roth |
| 5,445,617 A | 8/1995 | Yoon |
| 5,462,532 A | 10/1995 | Gresl |
| 5,466,224 A | 11/1995 | Yoon |
| 5,474,539 A | 12/1995 | Costa et al. |
| 5,478,317 A | 12/1995 | Yoon |
| 5,486,190 A | 1/1996 | Green |
| 5,522,833 A | 6/1996 | Stephens et al. |
| 5,527,335 A | 6/1996 | Bolduc et al. |
| 5,536,256 A | 7/1996 | Yoon |
| 5,549,564 A | 8/1996 | Yoon |
| 5,569,289 A | 10/1996 | Yoon |
| 5,569,293 A | 10/1996 | Yoon |
| 5,571,134 A | 11/1996 | Yoon |
| 5,573,511 A | 11/1996 | Yoon |
| 5,573,545 A | 11/1996 | Yoon |
| 5,575,804 A | 11/1996 | Yoon |
| 5,584,848 A | 12/1996 | Yoon |
| 5,584,849 A | 12/1996 | Yoon |
| 5,591,189 A | 1/1997 | Yoon |
| 5,591,190 A | 1/1997 | Yoon |
| 5,591,193 A | 1/1997 | Yoon |
| 5,603,719 A | 2/1997 | Yoon |
| 5,607,396 A | 3/1997 | Yoon |
| 5,607,439 A | 3/1997 | Yoon |
| 5,607,440 A | 3/1997 | Danks et al. |
| 5,618,271 A | 4/1997 | Yoon |
| 5,624,459 A | 4/1997 | Kortenbach et al. |
| 5,626,598 A | 5/1997 | Roth |
| 5,634,934 A | 6/1997 | Yoon |
| 5,637,096 A | 6/1997 | Yoon |
| 5,637,097 A | 6/1997 | Yoon |
| 5,645,076 A | 7/1997 | Yoon |
| 5,645,556 A | 7/1997 | Yoon |
| 5,645,557 A | 7/1997 | Yoon |
| 5,645,656 A | 7/1997 | Rubianes |
| 5,665,072 A | 9/1997 | Yoon |
| 5,665,102 A | 9/1997 | Yoon |
| 5,665,105 A | 9/1997 | Furnish et al. |
| 5,669,885 A | 9/1997 | Smith |
| 5,674,237 A | 10/1997 | Ott |
| 5,676,156 A | 10/1997 | Yoon |
| 5,676,681 A | 10/1997 | Yoon |
| 5,676,682 A | 10/1997 | Yoon |
| 5,676,683 A | 10/1997 | Yoon |
| 5,690,663 A | 11/1997 | Stephens |
| 5,707,362 A | 1/1998 | Yoon |
| 5,709,671 A | 1/1998 | Stephens et al. |
| 5,713,870 A | 2/1998 | Yoon |
| 5,730,755 A | 3/1998 | Yoon |
| 5,772,678 A | 6/1998 | Thomason et al. |
| 5,779,680 A | 7/1998 | Yoon |
| 5,797,943 A | 8/1998 | Danks et al. |
| 5,807,402 A | 9/1998 | Yoon |
| 5,810,866 A | 9/1998 | Yoon |
| 5,827,315 A | 10/1998 | Yoon |
| 5,843,115 A | 12/1998 | Morejon |
| 5,851,216 A * | 12/1998 | Allen ........................ 606/185 |
| 5,857,999 A | 1/1999 | Quick et al. |
| 5,868,773 A | 2/1999 | Danks et al. |
| 5,904,699 A * | 5/1999 | Schwemberger et al. .... 606/185 |
| 5,906,595 A | 5/1999 | Powell et al. |
| 5,916,232 A | 6/1999 | Hart |
| 5,993,470 A | 11/1999 | Yoon |
| 6,017,356 A * | 1/2000 | Frederick et al. ............ 606/185 |
| 6,030,402 A * | 2/2000 | Thompson et al. .......... 606/185 |
| 6,063,099 A | 5/2000 | Danks et al. |
| 6,238,407 B1 | 5/2001 | Wolf et al. |
| 6,319,266 B1 | 11/2001 | Stellon et al. |
| 6,478,806 B2 | 11/2002 | McFarlane |
| 6,497,716 B1 | 12/2002 | Green et al. |
| 6,613,063 B1 | 9/2003 | Hunsberger |
| 6,645,219 B2 | 11/2003 | Roe |
| 6,685,630 B2 | 2/2004 | Sauer et al. |
| 6,716,201 B2 | 4/2004 | Blanco |
| 6,719,746 B2 | 4/2004 | Blanco |
| 6,830,578 B2 | 12/2004 | O'Heeron et al. |
| 6,835,201 B2 | 12/2004 | O'Heeron et al. |
| 6,837,874 B1 | 1/2005 | Popov |
| 7,122,028 B2 | 10/2006 | Looper et al. |
| 2001/0029387 A1* | 10/2001 | Wolf et al. ................... 606/184 |
| 2003/0026207 A1 | 2/2003 | Loguinov |
| 2003/0032927 A1 | 2/2003 | Halseth et al. |
| 2003/0135229 A1 | 7/2003 | Green et al. |
| 2004/0243166 A1* | 12/2004 | Odermatt et al. ............ 606/185 |
| 2005/0070947 A1 | 3/2005 | Franer et al. |

* cited by examiner

TROCAR WITH RETRACTABLE CUTTING SURFACE

The present invention relates to a trocar and in particular to a trocar that has a retractable cutting surface such as a retractable cutting blade.

Trocars are surgical instruments that are used to puncture tissue to gain access to body cavities. Generally, a cannula surrounds at least a portion of the trocar so that after the tissue is punctured, the cannula can provide access to the body cavity for endoscopic instruments and the like. Common to many trocars is that sharp tip used to puncture the tissue is withdrawn or covered after the tissue is punctured and the trocar is removed from the site of the puncture.

One such example is shown in U.S. Pat. No. 5,474,539 where an obturator having an attached piercing tip is movable from a protected position within the cannula to an advanced or operative position distally of the cannula. After piercing the tissue, the obturator and attached tip are automatically withdrawn to a retracted position within the cannula. A disadvantage to this type of system is that there must be an operative connection between the obturator and the cannula, which complicates the system and increases its cost.

Another proposed solution provides a safety shield that covers the blade. The problem with this solution is that the incision must be sufficiently large so that the shield can cover the blade. In addition, the friction between the shield and the tissue must be reduced or eliminated; otherwise, the movement of the shield to cover the blade may be too slow.

Therefore, it would be beneficial to provide a trocar that does not rely on an operative connection with the cannula and does not need a cannula within which to withdraw the cutting surface in order to position the cutting surface in a safety position. The trocar according to the present invention solves that problem.

SUMMARY

According to the present invention a trocar is provided with a cutting surface, blade, or tip that is retractable within the obturator. Advantageously, the cutting surface will automatically retract into the obturator after the cutting surface penetrates through the tissue and the corresponding presence of pressure against the cutting surface is reduced or removed. The cutting surface quickly retracts so that contact or damage any internal organs is reduced or avoided In accordance with one embodiment of the present invention, a trocar is provided that comprises an outer housing, an inner housing, an obturator, a cutting shaft with a cutting surface at a distal end, and a spring that biases the cutting surface to an exposed position. The obturator is hollow with an open distal end and defines a longitudinal axis. The obturator surrounds the cutting shaft and cutting surface. The inner housing cooperates with the cutting shaft such that in a first position the cutting surface is retracted within the obturator and upon rotation of the inner housing from the first position, the cutting surface moves longitudinally with respect to the obturator to a second position wherein the cutting surface is exposed with the cutting surface located beyond the distal end of the obturator.

The cutting surface may have any known or suitable shape as is well known in the art or can be contemplated. In one embodiment, the cutting surface is removable from the cutting shaft. As a result, the cutting surface can be varied in its length, shape, or other features. Moreover, if the cutting surface is removable from the cutting shaft, a sharp surface can be provided as desired or needed.

Advantageously, the obturator is reusable, simple in construction, easy to clean, sterilize and maintain. Moreover, a cannula is not necessary for operation of the trocar so that the cannula is used to provide access for instrument insertion after penetration of the tissue.

DESCRIPTION

Figure 1:
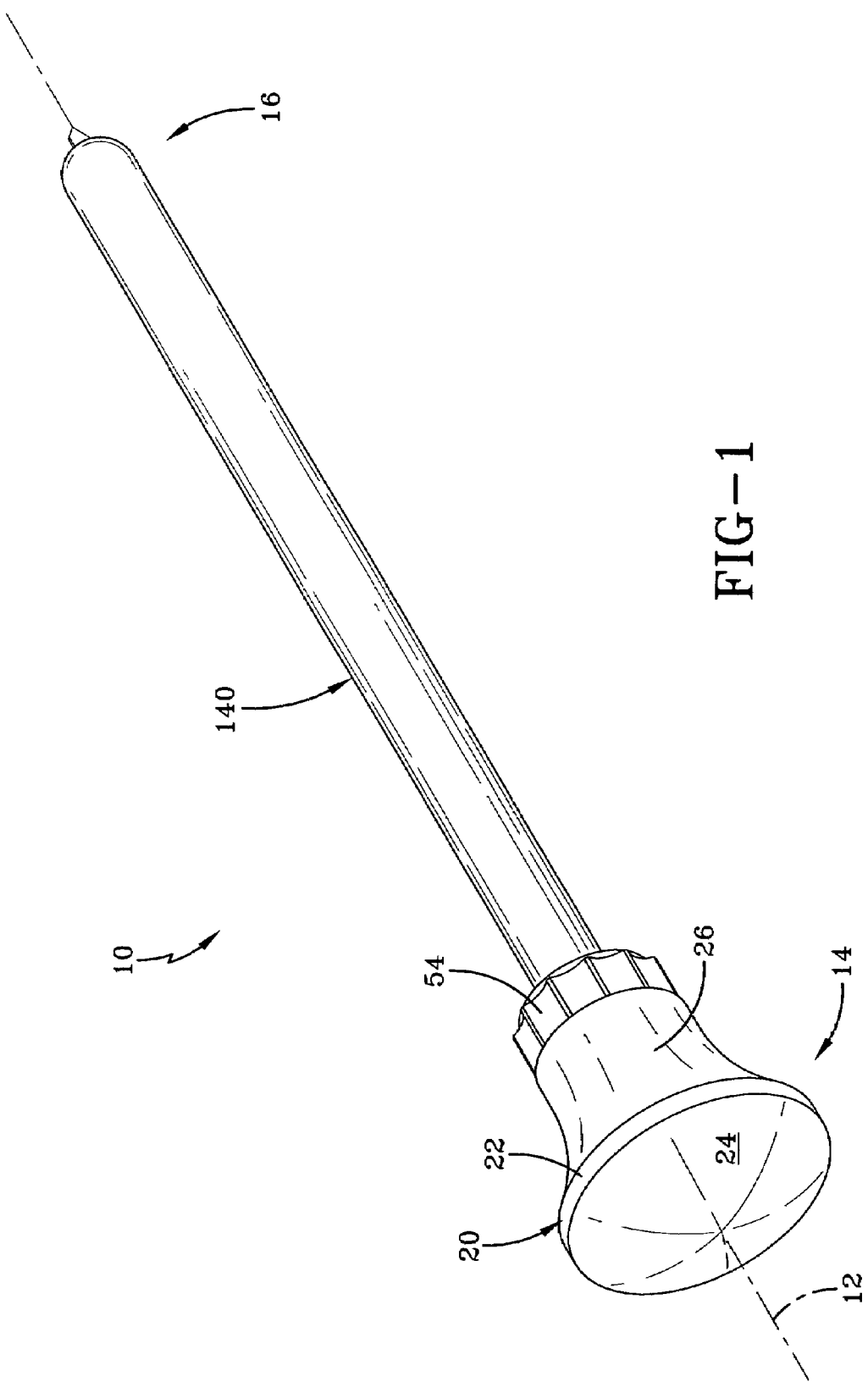
FIG. 1 is a perspective view of one embodiment of the trocar of the present invention.
Figure 2:
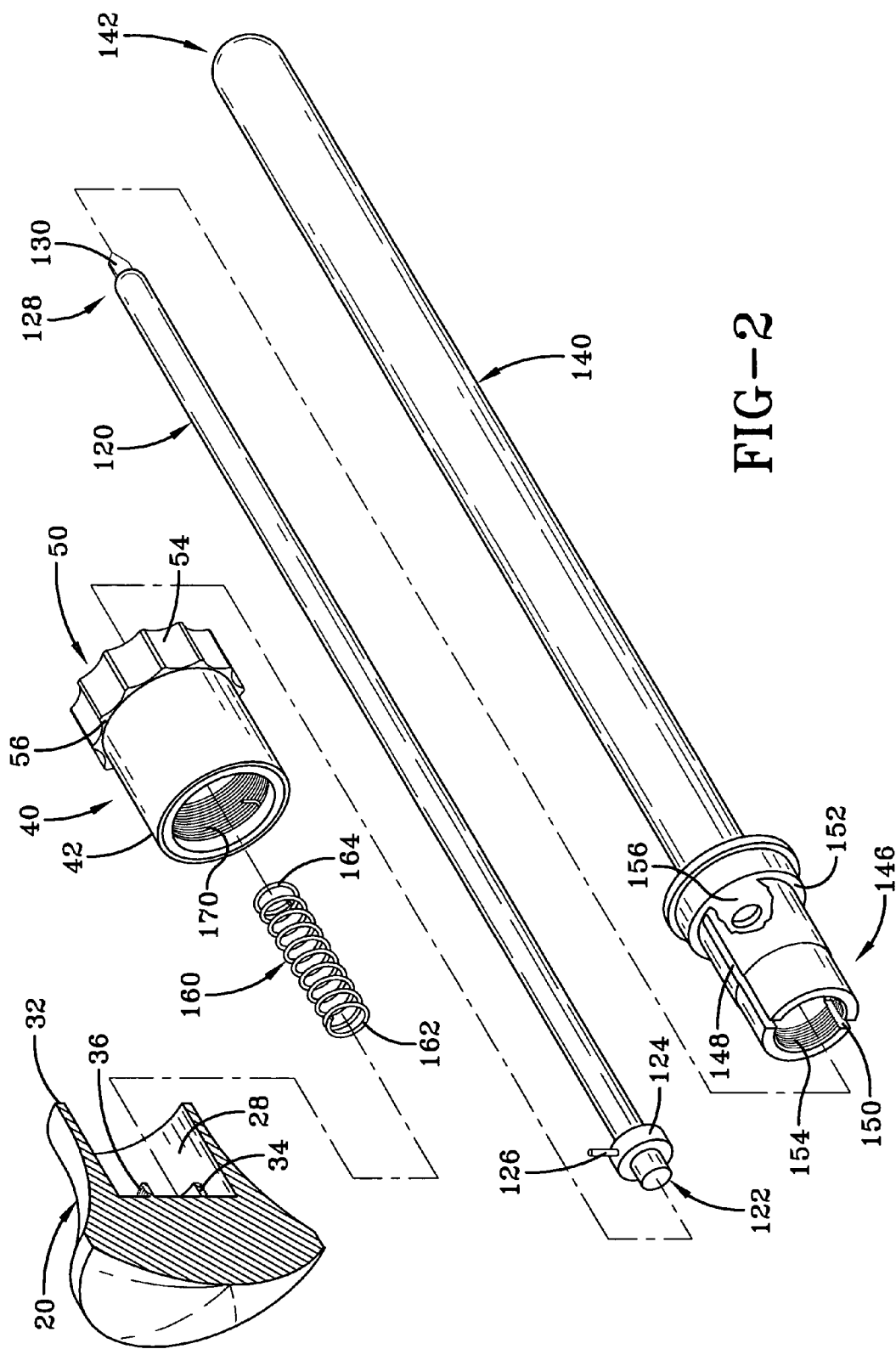
FIG. 2 is an exploded view of one embodiment of the trocar of the present invention with a portion of the outer housing exposed to show internal features of the outer housing.
Figure 3:
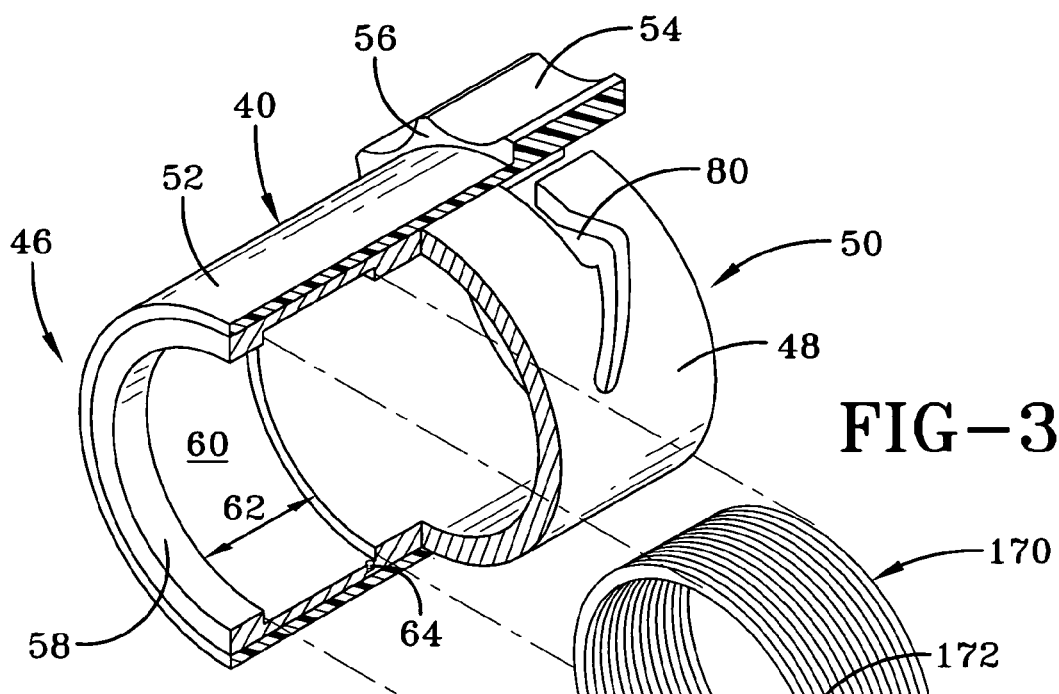
FIG. 3 is a partial cut-away view of the inner housing and with the second spring shown in exploded view with a portion of the spring being cut away to show one end of the spring.
Figure 4:
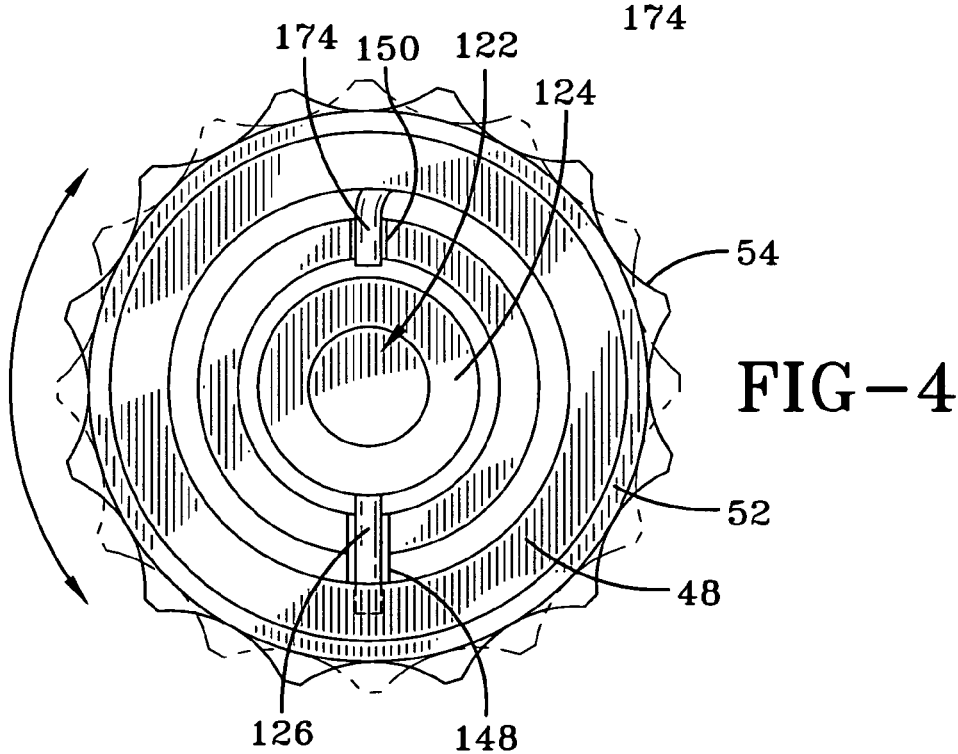
FIG. 4 is an end view of the proximal end of the trocar with the outer housing removed to better illustrate features of the present invention.

Turning now to FIGS. 1 and 2, a trocar 10 of the present invention is shown. The trocar 10 includes an outer housing 20, an inner housing 40, a cutting shaft 120 that carries a cutting surface 130, an obturator 140 that surrounds the cutting shaft 120 and from which the cutting surface 130 extends, a first spring 160, and a second spring 170. The trocar 10 may be described as being aligned along a longitudinal axis 12 and having a proximal end 14 and a distal end 16. The proximal end 14 is the end of the trocar 10 defined by the outer housing 20 and the distal end 16 is the end of the trocar 10 from which the cutting surface 130 extends from the obturator 140.

The outer housing 20 has an outer surface 22 and an inner surface 28. The outer surface 22 may have any shape suitable for grasping. Accordingly, the outer housing 20 as shown in FIG. 1 has a convex top portion 24 with a tapered sidewall 26. The outer housing 20 can be made of any material suitable for a sterile environment. The inner surface of the outer housing 20 is cylindrical and has a diameter slightly larger than at least a portion of the outer surface 42 of the inner housing so that the outer housing 20 can surround the inner housing 40.

A flange 34 extends from an inner portion of the outer housing 20 and contains threads 36 on its periphery that will threadably engage threads 154 provided on the inner portion of the proximal end 146 of the obturator. As will become clear from the discussion below, the flange 34 also receives one end 162 of a spring 160.

As best seen in FIG. 2, the inner housing 40 is desirably cylindrically shaped and has an outer surface 42, an inner surface 58, a first (or proximal) end 46, and a second (distal) end 50. The inner housing 50 may be formed of two pieces, an inner piece 48 and an outer piece 52. When formed of two pieces, each piece may be formed of a single material or of differing materials. In addition, when formed of two pieces the pieces are securely joined or attached such that movement of the outer piece 52 results in movement of the inner piece 48 and vice versa. Alternatively, the inner housing 50 may be formed of a single piece.

In one embodiment, at least a portion of the outer surface 42 adjacent the second end 50 defines a flange 56. The distal end 32 of the outer housing 20 may abut the flange 56. The outer surface of the second end 50 of the inner housing desirably has a gripping surface 54 so that the inner housing 40 can be grasped and rotated. The gripping surface 54 can have any suitable form or material. For example, the gripping surface 54 may be in the form of scalloping.

The inner surface 58 of the inner housing 40 has a groove 60 that circumscribes the inner surface 58 of the inner housing 40. The groove 60 is located adjacent the proximal end 46 of the inner housing. The groove 60 receives a spring 170, desirably a torsion spring such as a radial torsion spring. Therefore, the groove 60 has a width 62 that is about the same size as the width of the torsion spring. In addition, an aperture 64 is provided and it receives one end 172 of the spring.

The inner housing 40 cooperates with the cutting shaft 120 such that when the inner housing 40 is in a first position, the cutting surface 130 is retracted and when the inner housing 40 rotates to a second position, the cutting shaft 120 and the cutting surface 130 move laterally such that the cutting surface 130 is exposed. Referring back to FIG. 2, the cutting shaft 120 has a proximal end 122 and a distal end 128. The distal end 128 carries a cutting surface 130. The cutting surface 130 may have any known or suitable shape as is well known in the art or can be contemplated. In one embodiment, the cutting surface 130 is removable from the cutting shaft 120. As a result, the cutting surface 130 can be varied in its length, shape, or other features. The proximal end 122 has a flange 124 that surrounds the outer surface of the cutting shaft. Desirably, the flange includes a pin 126 that is received within a cam slot 80 provided on the inner housing 40 as described below.

The cam slot 80 is located adjacent the distal end 50 of the inner housing 40. The cam slot 80 is provided on the inner surface 58 of the inner housing 40. Although the cam slot 80 can extend from the inner surface 58 to the outer surface 42, it is desired that the cam slot 80 does not extend through to the outer surface because it will reduce the amount of surface that can become dirty or contaminated or caught by the operator.

The cam slot 80 has at least two portions 82, 92 defining two positions, e.g., a first position where the cutting surface 130 is retracted, i.e., not exposed and a second position where the cutting surface 130 is exposed. In one embodiment, the cam slot 80 has three portions 82, 92, 98 defining three positions. The first 82 and second portions 92 are the same as described above. The third portion 98 defines a position when pressure is exerted in a proximal direction against the cutting surface 130.

Figure 7:
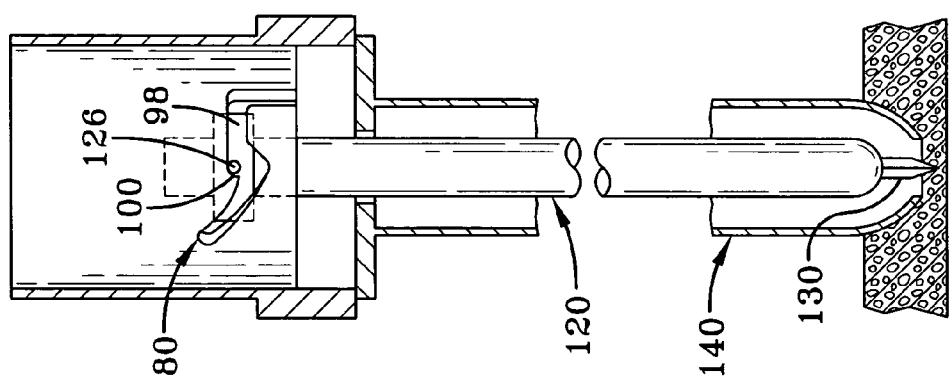
FIG. 7 is a partial cross sectional view of the trocar with the cutting surface in a deployed or operative position and piercing the tissue and where the obturator has entered the tissue opening. Elements have been removed to better show the operation of the cutting mechanism within the obturator and the pin within the cam slot of the inner housing.
Figure 6:
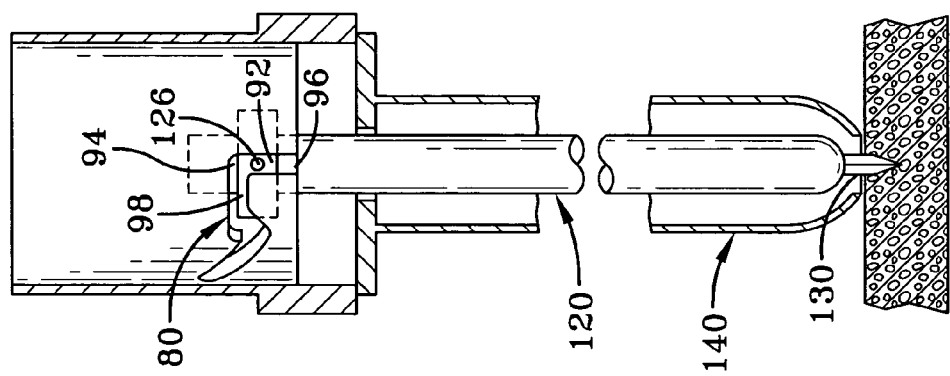
FIG. 6 is a partial cross sectional view of the trocar with the cutting surface in a deployed or operative position and piercing the tissue but where the obturator has not yet entered the tissue opening. Elements have been removed to better show the operation of the cutting mechanism within the obturator and the pin within the cam slot of the inner housing.
Figure 5:
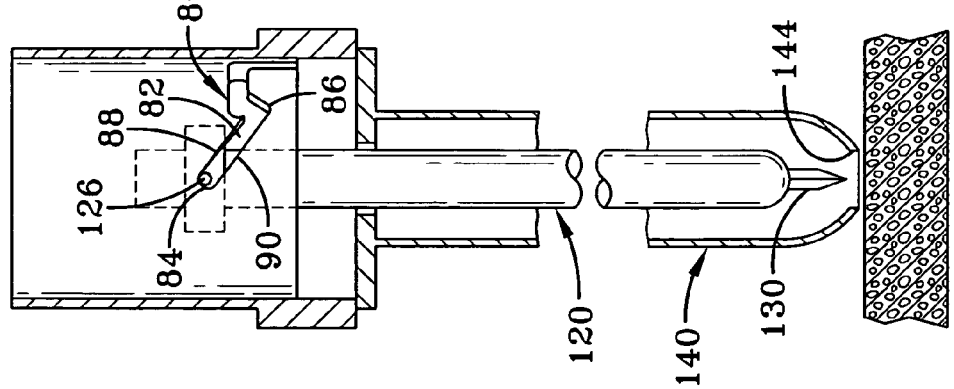
FIG. 5 is a partial cross sectional view of the trocar with the cutting surface in a retracted position within the obturator. Elements have been removed to better show the operation of the cutting mechanism within the obturator and the pin within the cam slot of the inner housing.

As better seen in FIGS. 5-7, in one embodiment of the trocar 10 of the present invention, the cam slot 80 has a first portion 82, a second portion 92, and a third portion 98. The first portion 82 has a first end 84, a second end 86, a proximal surface 88, a distal surface 90, and is angled from the longitudinal axis 12 such that when the pin 126 is at the first end 84 of the first portion 82, the cutting shaft 120 is in the furthest proximal position. In this, the first position, the cutting surface 130 is retracted into the obturator 140 as shown in FIG. 5. The first portion 82 may have any suitable angle from the longitudinal axis depending on the force desired to return the cutting surface to the first position.

The second portion 92 has a first end (a proximal position) 94, a second end (a distal position) 96. The second end 96 is open at the distal end 50 of the inner housing 40 so that the pin 126 can engage the cam slot 80. In other words, in order to assemble the trocar 10, the second end 96 of the second portion 92 is open so that the pin 126 can slide into the cam slot 80. In use, despite the fact that the second or distal end 96 of the second portion 92 is open, the cutting shaft 120 is stopped from distal movement when the flange 124 on the cutting shaft 120 contacts an inner flange 156 on the obturator 140. When the pin 126 is in the distal end 96 of the second portion, the cutting surface 130 is exposed, i.e., the cutting surface 130 extends from the distal end 142 of the obturator 140 as best seen in FIG. 6, which is referred to as the second position.

The third portion 98 of the cam slot 80 connects the first portion 82 with the second portion 92 and is aligned normal to the longitudinal axis 12. The third portion 98 has a stop 100 that is adjacent the distal end 86 of the proximal surface 88 of the first portion 82. When the pin 126 is in the second position, the cutting surface 130 is exposed and pressure has been applied to the cutting surface 130 in a proximal direction such as by, for example, tissue or tissue body that the cutting surface 130 is penetrating. As a result, the pin 126 has traveled from the second portion 92 to the third portion 98 and is held by the stop 100 so that the cutting surface 130 can penetrate or cut the tissue or other material, as best seen in FIG. 7, which is referred to as the third position.

An obturator 140 surrounds the cutting shaft 120 and, when the cutting shaft 120 is in the first position, the cutting surface 130 is completely withdrawn inside the obturator 140. The obturator 140 has a distal end 142, from which the cutting surface 130 extends, and a proximal end 146, which cooperates with the proximal end 122 of the cutting shaft 120 and the inner housing 40. At least one longitudinal slot 148 is provided at the proximal end 146 of the obturator 140. Desirably, a first longitudinal slot 148 and a second longitudinal slot 150 are provided at the proximal end 146 of the obturator 140. The second slot 150 may be provided at any suitable location relative to the first slot 148. In some embodiments, the second slot 150 is opposite the first slot 148.

The first slot 148 receives the pin 126 provided on the cutting shaft 120 and the pin extends outwardly from the obturator 140. The first longitudinal slot 148 extends from the proximal end 146 of the obturator 140 toward the distal end 142 of the obturator 140. The first longitudinal slot 148 extends a distance such that when the pin 126 abuts the distal end of the slot 148, the cutting surface 130 is exposed a desired distance from the distal end 142 of the obturator 140.

The second longitudinal slot 150 receives one end 174 of the second spring 170. The second longitudinal slot 150 extends from the proximal end 146 of the obturator 140 toward the distal end 142 of the obturator.

A flange 152 is provided adjacent the proximal end 146 of the obturator 140. The flange 152 may act as a stop for the inner housing 40 and to limit the distance the inner housing 40 can slide in a distal direction.

As noted above, a first spring 160 is provided and it is desirably a coil spring having a first end 162 and a second end 164. The first end 162 is received within the flange 34 provided on the inner surface 28 of the outer housing 20 opposite the top of the outer housing 24. The second end 164 abuts the flange 124 provided on the cutting shaft 120 to bias the cutting shaft 120 in a distal direction, i.e., in a direction such that the cutting surface 130 will be in an exposed position. If desired, the second end 164 may be fixed to the flange 124 on the cutting shaft 120.

The trocar 10 also has a second spring 170, desirably in the form of a torsion spring, such as a radial torsion spring. The second spring 170 has a first end 172 that extends outward from the spring 170 and is received in an aperture 64 provided in the groove 60 of the inner surface 58 of the inner housing 40. The second end 174 extends inward from the spring 170 and is received in the at least one of the longitudinal slots 148, 150 of the obturator 140. Desirably, the second end 174 extends into the second longitudinal slot 150.

It will be understood by one of skill in the art that because the first 172 and second 174 ends of the second spring 170 are retained in a position relative to each other that the inner housing 40 will be biased to a first position. In addition, rotation of the inner housing 40 will act against the spring tension or force of the second spring 170. The second spring can be manufactured to provide a suitable force or torque. In one embodiment, the spring provides a torque at 90° in the range from about 20 to about 40 N·mm, suitably in the range from about 24 to about 31 N·mm.

Operation of the trocar 10 will now be described. FIG. 5 shows the safety position of the trocar 10 with the cutting surface 130 disposed within the obturator 140. In this position, the cutting shaft 120 is retracted to its most proximal position and the pin 126 is at the first end 84 of the first portion 82 of the cam slot 80. In a desired embodiment, the tension or spring force of the second spring 170 is greater than the spring force of the first spring 160. Because the force of second spring 170 overcomes the force of the first spring 160, which biases the cutting surface 130 to an exposed position, the inner housing 40 is biased to the position shown in FIG. 5. In addition, because the inner housing 40 is biased to the position shown in FIG. 5, the pin 126 is at the first end 84 of the first portion 82 of the cam slot 80 and thus, the cutting shaft 120 is at its most proximal position.

To actuate and expose the cutting surface 130 from the distal end 142 of the obturator 140, the inner housing 40 is rotated to the position shown in FIG. 6. As a result, the pin 126 travels downwardly in the first portion 82 of the cam slot 80, across the third portion 98 and into the second portion 92 of the cam slot 80. Although the second spring 170 acts to bias the inner housing 40 to the position shown in FIG. 5, the wall of the second portion 92 of the slot 80 prevents the inner housing 40 from rotating. In this position, the first spring force 160 biases the cutting surface 130 to an exposed position with the cutting surface 130 extending beyond the distal end 142 of the obturator 140. The cutting surface 130 will distally extend a distance dictated by either the length of the first spring 160, the flange 152 provided on the obturator 140, or a combination of both.

The cutting surface 130 is now ready to be used. When the cutting surface 130 contacts, for example, the tissue body of the abdominal wall, pressure is exerted in a proximal direction against the cutting surface 130. The spring force of the first spring 160 is such that it is less than the pressure required to penetrate the tissue body and is such that the pin 126 moves to the proximal position 94 of the second portion 92 of the cam slot 80. In this position, the inner housing 40 is not constrained from rotational movement by the pin 126 in the third portion 98 of the cam slot 80 and therefore, the inner housing 40 rotates in a direction such that the pin 126 moves toward the first portion 82 of the cam slot 80. The pin 126 moves along the third portion 98 of the cam slot 80 until it contacts the stop 100. The pin 126, cutting shaft 120, and cutting surface 130 remain in this position until the pressure against the cutting surface 130 is reduced to a degree or by an amount such that it is less than the distally biasing force of the first spring 160 or is removed.

As noted above, the angle of the first portion 82 of the cam slot 80 will determine the amount of force that the second spring 170 must provide to overcome the biasing force of the first spring 160 and move the cutting shaft 120 and pin 126 to the proximal end 84 of the cam slot 80. In other words, the greater the angle of the first portion 82, the greater the force that the second spring 170 must provide. Likewise, the smaller the angle of the first portion 82, the lower the force that the second spring 170 must provide.

Figure 8:
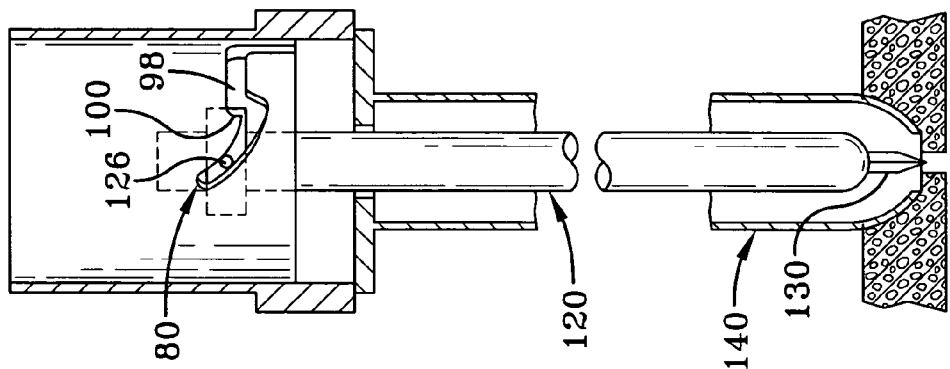
FIG. 8 is a partial cross sectional view of the trocar with the cutting surface blade after penetration through the tissue and in a partially retracted position within the obturator. There is no force applied to the cutting surface and the obturator is shown as partially entering the tissue opening. Elements have been removed to better show the operation of the cutting mechanism within the obturator and the pin within the cam slot of the inner housing.

When the pressure against the cutting surface 130 is reduced to a degree or by an amount such that it is less than the distally biasing force of the first spring 160 or is removed (e.g. when the cutting surface 130 completely penetrates the tissue), the first spring 160 biases the cutting shaft 120 (and thus the pin 126) in a distal direction. As a result, the pin 126 is moved from the stop 100 and, because the force of the second spring 170 is greater than the force of the first spring 160, the inner housing 40 rotates such that the pin 126 travels in a proximal direction along the first portion 82 of the cam slot 80 as best seen in FIG. 8 until the pin 126 reaches the proximal position 84 of the first portion 82 of the cam slot 80, as best seen in FIG. 5. The cutting surface 130 is then in its fully retracted position (the safety position). Thus, the cutting surface quickly retracts so that the cutting surface does not contact or damage any internal organs, blood vessels, or unintended areas.

It will be appreciated that during operation of the trocar 10 that the inner housing 40 rotates but does not move laterally and that the cutting shaft 120 moves laterally but does not rotate. In addition, the trocar 10 of the present invention provides a cutting surface 130 that immediately and automatically retracts after the cutting surface 130 has penetrated the tissue body. In other words, after the manual actuation of the cutting surface 130 to expose the cutting surface 130 to a use position (the second position), the retraction of the cutting surface 130 to a retracted or safety position is immediate and automatic.

Figure 9:
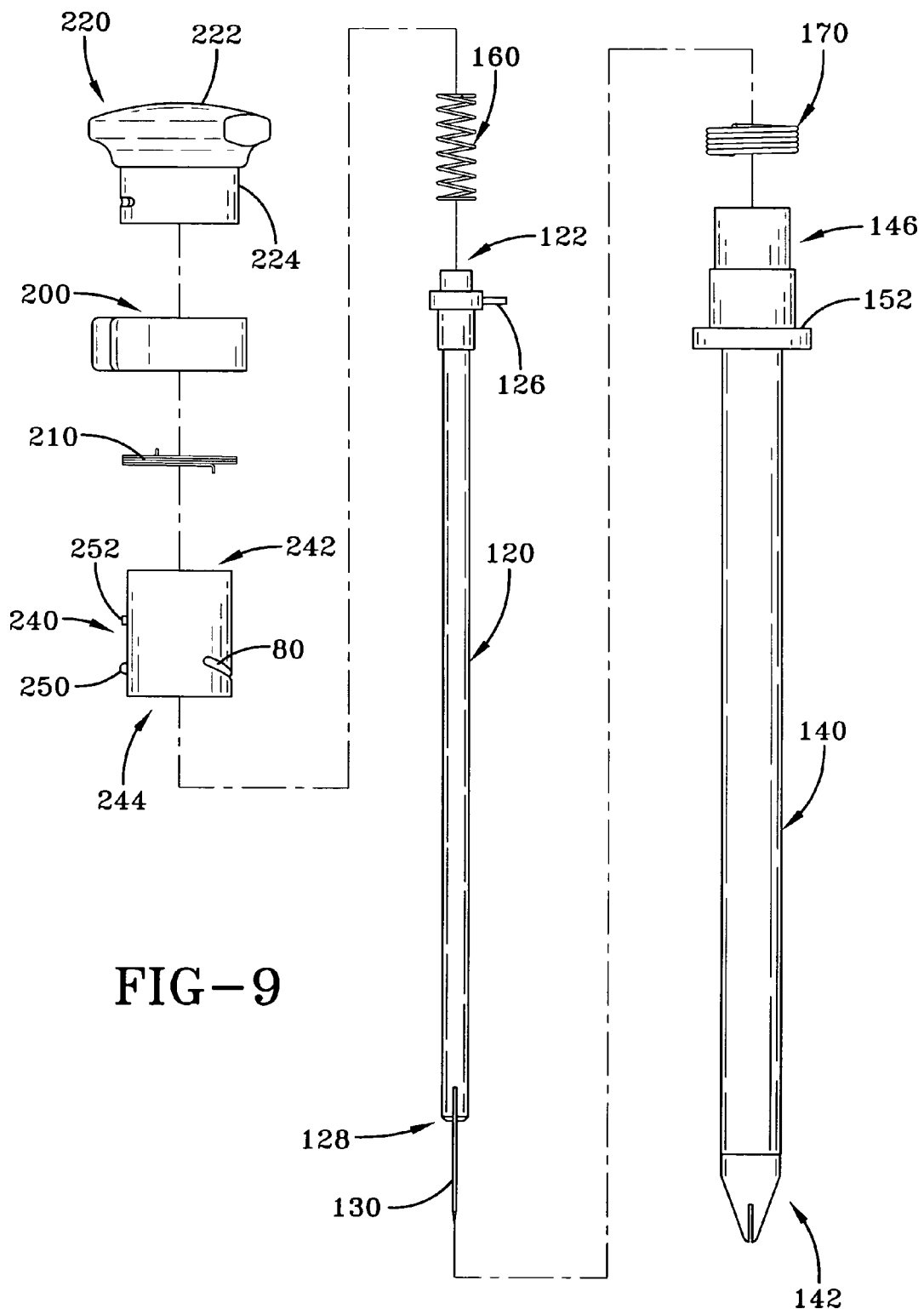
FIG. 9 is an exploded view of another embodiment of the trocar of the present invention.
Figures 10, 11, 12:
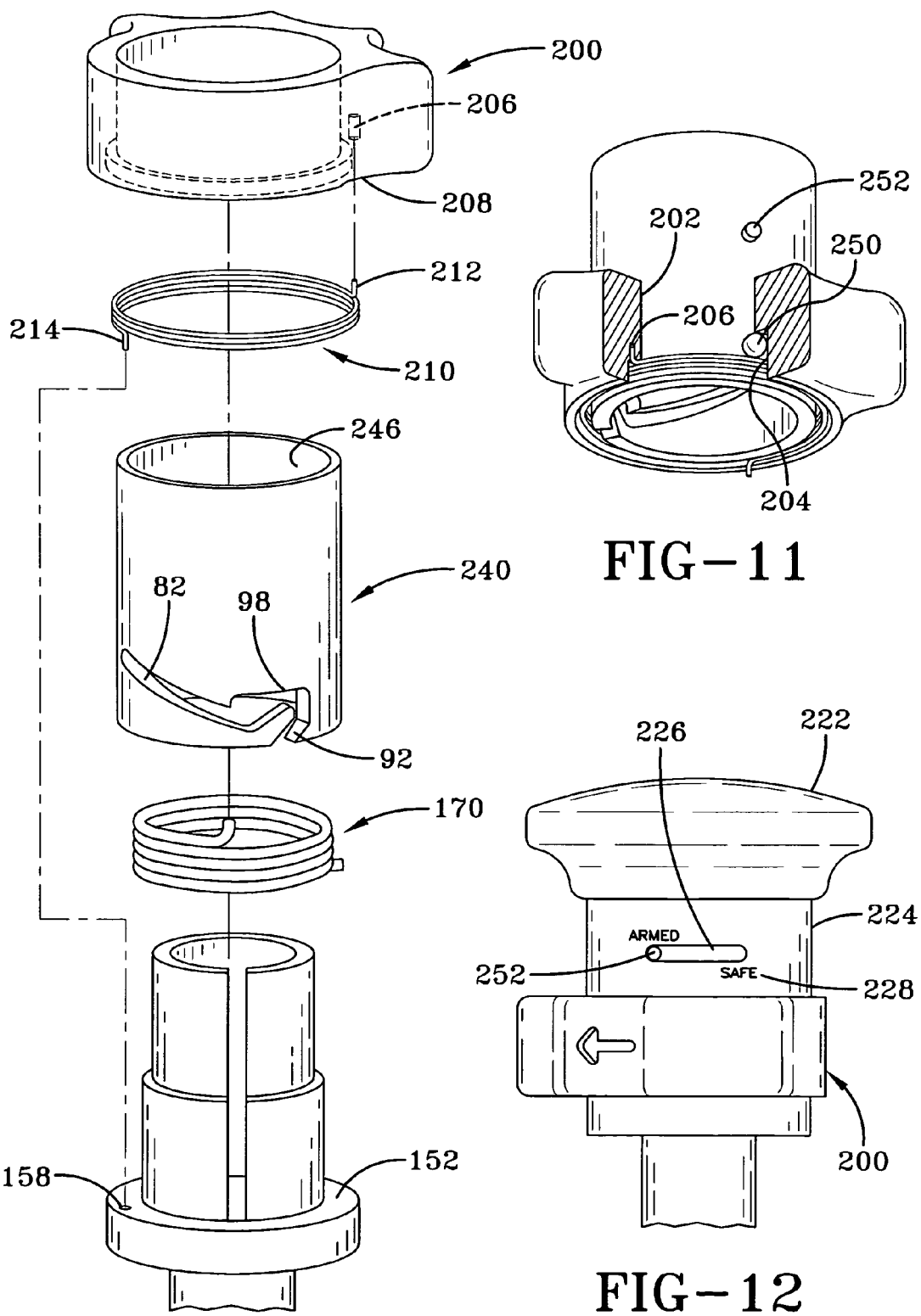
FIG. 10 is an exploded view of a portion of the trocar of FIG. 9 and, in particular the proximal end of the trocar to show the relationship of the proximal end of the cutting shaft, the inner housing, the return spring and the actuation ring.
FIG. 11 is a perspective view of a portion of the inner housing of one embodiment with a portion cutaway to better show features of the present invention. In particular, the inner housing is shown with the actuation ring and return spring in position.
FIG. 12 is a side view of the outer housing of one embodiment to show the actuation ring and the outer housing indicator.

Turning now to FIG. 9 another embodiment of the present invention is illustrated. In describing this embodiment like reference numerals will be used to identify like parts. As with the previously described embodiment, the trocar 10 is provided with an outer housing 220, an inner housing 240, a cutting shaft 120 that carries a cutting surface 130, an obturator 140 that surrounds the cutting shaft 120. In addition, the trocar includes an actuation ring 200 and a return spring 210. As with the previously described embodiment, the cutting shaft 120, the obturator 140, the first spring 160 and the second spring 170 in this embodiment function in the same manner as the previously described embodiment. In this embodiment, the outer housing 220 has a top portion 222 and a sidewall 224 extending from the top portion. The top portion 222 and sidewall 224 may be separate pieces or may be a single unitary piece. The sidewall 224 is provided with a slot 226 that is preferably substantially laterally oriented (best seen in FIG. 12). Adjacent the slot 226, icons 228 may be located to provide a visual indication of the state of the cutting surface 130. In other words, the icons 228 may indicate whether the cutting surface 130 is in an extended or a retracted position.

The inner housing 240 has a first or proximal end 242 and a second or distal end 244. The distal end 244 of the inner housing is contiguous with the flange 152 of the obturator 140. As with the inner housing of the other embodiments, the inner surface 246 of the inner housing 240 has a groove (not shown) that circumscribes the inner surface 246 of the inner housing 240 to receive the second spring 170 in the same manner as with the inner housing 40.

The inner housing 240 is provided with a cam slot 80 located adjacent the distal end 244 of the inner housing 240. The cam slot 80 is provided on the inner surface of the inner housing 40. Although the cam slot 80 can extend through the entire wall of the inner housing, it is not necessary that the cam slot 80 does so. Accordingly, the cam slot 80 may be provided only on the inner surface 246 of the inner housing, which will reduce the amount of surface that can become dirty or contaminated or caught by the operator. Alternatively, the actuation ring 200 can be located so that the actuation ring 200 covers the cam slot 80.

The cam slot 80 has at least two portions 82, 92 defining two positions, e.g., a first position where the cutting surface 130 is retracted, i.e., not exposed and a second position where the cutting surface 130 is exposed. In one embodiment, the cam slot 80 has three portions 82, 92, 98 defining three positions. The first 82 and third portions 98 are the same as described above. The second portion 92 in the inner housing 240 is angled. Desirably, the angle is in a direction opposite that of the travel of the pin 126 as the pin travels from the cutting surface extended position to the cutting surface retracted position.

The inner housing 240 is also provided with a first radially extending pin 250 and a second radially extending pin 252 spaced from the first radially extending pin. The first radially extending pin engages a slot 202 provided in the inner surface 202 of the actuation ring 200 to drivingly connect the actuation ring 200 to the inner housing 240. The slot 204 extends around a portion of the inner surface 202 of the actuation ring 200, the purpose of which will become clear from the following text. Alternatively, the pin may be dispensed with and the actuation ring 200 may be drivingly connected to the inner housing in another conventional manner. Or, the actuation ring and the inner ring may be formed as a single piece.

The second radially extending pin 252 extends through the slot 226 of the side wall 224 of the outer housing 220. The second radially extending pin 252 can therefore provide a visual indication whether the cutting surface 130 is in an extended or a retracted position. It will be understood by those of skill in the art, that the second radially extending pin 252 in conjunction with the icons 228 can provide an enhanced visual indication.

As noted above, a return spring 210 is provided. The return spring is provided with a first end 212 and a second end 214. The first end 212 engages a cavity 206 formed on the bottom 208 of the actuation ring 200. The second end 214 engages a cavity 158 formed on the flange 152 of the obturator 140. When the first end 212 and the second end 214 are received in their respective cavities, the actuation ring 200 will be biased toward a rest position. In practice, the actuation ring 200 is drivingly connected to the inner housing 240 by the engagement of the pin 250 in the slot 204 so that the shaft 120 and thus the cutting surface 130 will be in the retracted position (indicated with the icon 228 "safe" in FIG. 12).

To actuate and expose the cutting surface 130 from the distal end 142 of the obturator 140, the actuation ring 200 is rotated to drivingly rotate the inner housing 240 such that the pin is in the second portion 92 of the cam slot 80. In other words, as the actuation ring 200 is rotated, one end wall (not shown) of the slot 204 contacts the first radially extending pin 250 to drivingly rotate the inner housing 240. The second radially extending pin moves from one end of the slot 226 (indicated with the icon 228 "safe" in FIG. 12) to the other end of the slot (indicated with the icon 228 "armed" in FIG. 12). The cutting surface 130 is then exposed. When the force rotating the actuation ring 200 is released, the actuation ring 200 is biasingly moved to its rest position, while the inner housing 240 remains in position because the slot 204 rides over the pin 250 without moving the inner housing 240.

Figure 13:
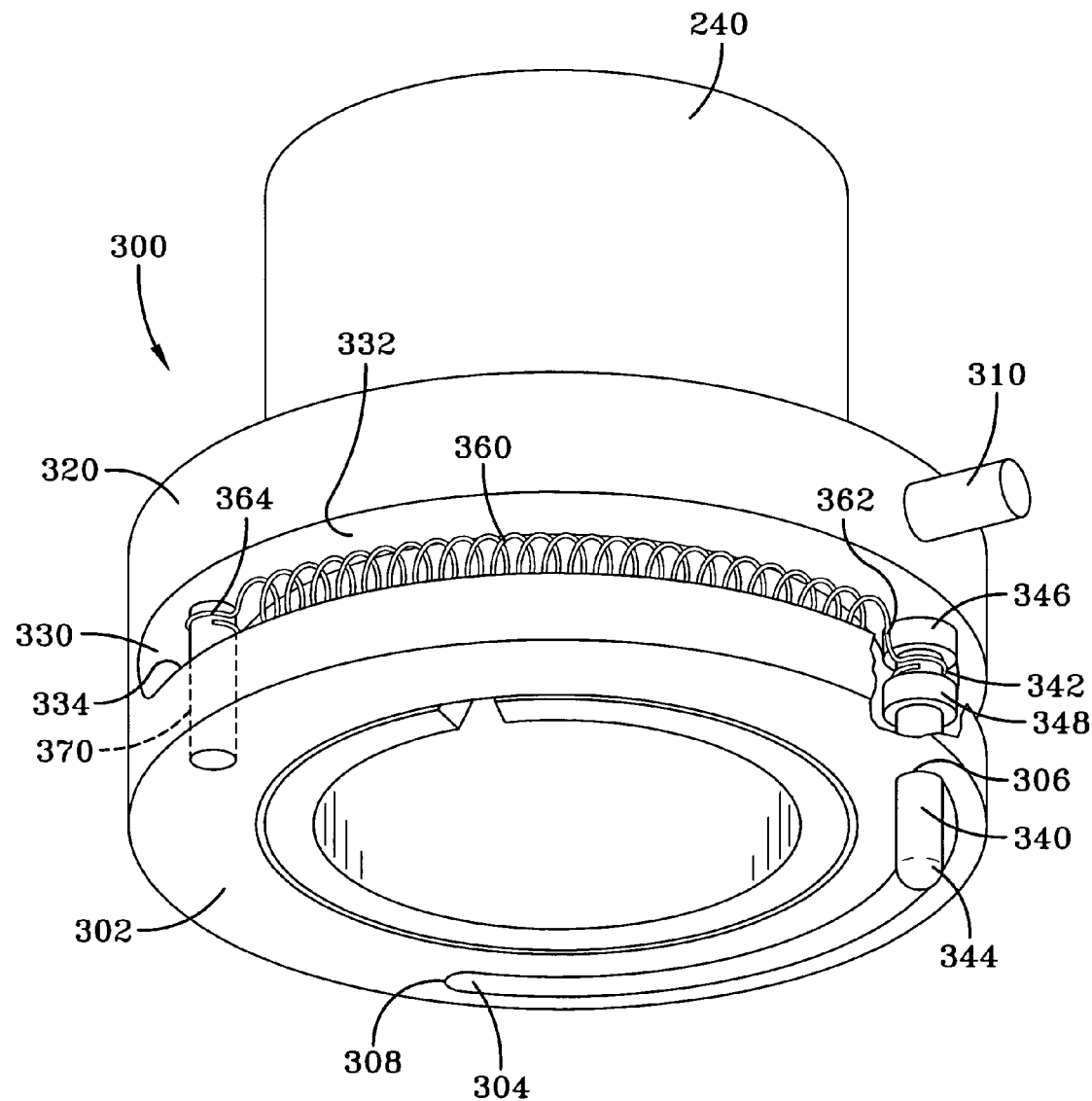
FIG. 13 is a side view of one embodiment of an inner housing and an intermediate member.

Referring to FIG. 13, another embodiment of a portion of the trocar of the present invention is shown. In FIG. 13, a portion of the inner housing 240 is shown with an intermediate member 300 surrounding the inner housing 240. The intermediate member 300 may be integrally formed as or with the actuation ring (not shown) or it may be separate from the actuation ring. When the intermediate member 300 is separate from the actuation ring, the actuation ring may be fixed to the intermediate member in any suitable manner such as by press fitting or the like.

As with the inner housing 240 of the other embodiments, the inner surface of the inner housing has a groove (not shown) that circumscribes the inner surface of the inner housing to receive the second spring 170 in the same manner as with the other inner housings. In addition, the inner housing is provided with a cam slot (not shown) as described in connection with the other inner housings.

The intermediate member 300 surrounds the inner housing and in general surrounds the distal portion of the inner housing. The intermediate member 300 has a radially extending pin 310 that rides in the slot 204 of the actuation ring 200. The intermediate member radially extending pin 310 is also attached to the inner housing 240 in any suitable manner so that movement of the intermediate member 300 causes corresponding movement of the inner housing 240.

The intermediate member 300 is provided with a peripheral groove 330 about a portion of the outer periphery 320. In addition, the bottom 302 of the intermediate member 300 is provided with a slot 304 that extends about a portion of the circumference of the bottom 302 of the intermediate member 300. The slot has a first end 306 and a second end 308. A traveling pin 340 has a first end 342 extending in the groove and a second end 344 that extends through the slot 304 and engages the cavity 158 formed on the flange 152 of the obturator 140.

The traveling pin 340 is biased to a position adjacent the first end 306 of the slot 304 by a biasing member 360. The biasing member 360 can have one end 362 attached to the traveling pin 340 and a second end 364 attached to a portion of the intermediate member 300. As shown in FIG. 13, a stationary pin 370 is provided to secure a second end 364 of the biasing member 360. The biasing member 360 can have any suitable form and is shown as a coil spring in FIG. 13.

The first end 342 of the traveling pin 340 may be provided with a first 346 and a second shoulder 348 that will aid in the travel of the traveling pin 340 in the groove 330. In this regard, the first shoulder 346 may be adjacent one wall 332 of the groove and the second shoulder 348 may be adjacent the opposite wall 334 of the groove. Where a first 346 and second 348 shoulder is provided, one end 362 of the biasing member 360 may be attached to the traveling pin 340 in the area between the first 346 and second 348 shoulder.

When the second end 344 of the traveling pin 340 is received in the cavity 158, the actuation ring 200 will be biased toward a rest position. In practice, the actuation ring 200 is drivingly connected to the inner housing 240 by the engagement of the intermediate member radially extending pin 310 with the inner housing 240 and with the slot 204 of the actuation ring 200 so that the shaft 120 and thus the cutting surface 130 will be in the retracted position (indicated with the icon 228 "safe" in FIG. 12).

To actuate and expose the cutting surface 130 from the distal end 142 of the obturator 140, the actuation ring 200 is rotated to drivingly rotate the inner housing 240 such that the pin 126 is in the second portion 92 of the cam slot 80. In other words, as the actuation ring 200 is rotated, one end wall (not shown) of the slot 204 contacts the intermediate member radially extending pin 310 to drivingly rotate the inner housing 240. When the force rotating the actuation ring 200 is released, the actuation ring 200 is biasingly moved to its rest position by the biasing member 360, while the inner housing 240 remains in position because the slot 204 rides over the intermediate member radially extending pin 310 without moving the inner housing 240.

It is to be understood that, while the invention has been described above in conjunction with the specific embodiments, the description is intended to illustrate and to limit the scope of the present invention, which is defined by the scope of the claims. For example, while several or the parts have been described as being formed as separate parts, it is possible to form them as a single piece. Advantageously, one of skill in the art will understand that the trocar 10 of the present invention will operate independently of a cannula, although the use of a cannula with the trocar 10 is contemplated. The cannula may surround the proximal end of obturator and, after penetration of the tissue body (e.g., the abdominal wall), the cutting surface will retract into the obturator (but not into the cannula), the cannula can be placed, and the trocar can be withdrawn from the cannula to provide an access port, as is known in the art.

The invention claimed is:

1. A trocar comprising:
a cutting shaft with a cutting surface at a distal end;
a hollow obturator defining a longitudinal axis and having an open distal end, the obturator surrounding the cutting shaft and cutting surface;
a spring urging the cutting surface to an exposed position;
a housing cooperating with the cutting shaft wherein, in a first position, the cutting surface is retracted within the obturator and, upon rotation of the housing in about an axis that is parallel to the longitudinal axis from the first position, the cutting surface moves axially relative to the obturator to a second position wherein the cutting surface is exposed;
an obturator longitudinal slot extending from a proximal end of the obturator toward the distal end;
a flange provided on the cutting shaft and a pin extending radially outward from the cutting shaft flange, wherein the pin cooperates with the obturator longitudinal slot to secure the cutting shaft from rotational movement relative to the obturator;
an obturator flange provided on the obturator spaced from the proximal end such that the longitudinal slot extends from the proximal end to the obturator flange; and
a cam slot provided on an inner surface of the housing to receive the pin.

2. The trocar of claim 1 wherein the housing has a first end that contacts the obturator flange.

3. The trocar of claim 1 wherein the cam slot has a shape to define at least two positions such that, when the pin is in a first position of the cam slot, the cutting surface is retracted within the obturator and upon rotation of the inner housing, the pin moves to a second position of the cam slot such that the cutting surface moves laterally with respect to the obturator to the exposed position.

4. The trocar of claim 3 wherein the cam slot has three positions such that when pressure against the cutting surface exists, the cutting shaft moves in a proximal direction causing the pin to move to a third position in the cam slot.

5. The trocar of claim 4 wherein when the pressure against the cutting surface is removed, the pin moves to the first position in the cam slot.

6. A method of cutting tissue comprising the steps of:
providing a trocar in accordance with claim 1;
actuating the housing to expose the cutting surface from the distal end of the obturator;
penetrating tissue with the cutting surface by applying pressure to a tissue that provides a tissue resistance; and
automatically retracting the cutting surface within the distal end of the obturator in response to a decrease in the tissue resistance.

7. The method of claim 6 wherein the cutting surface is automatically retracted within the obturator in response to an absence of tissue resistance.

8. The method of claim 6 wherein the cutting surface is automatically retracted within the obturator when the cutting surface completely penetrates the tissue.

9. The method of claim 6 wherein the step of actuating the housing comprises a rotational movement of the housing.

* * * * *